US007769215B2

(12) United States Patent
Horsch et al.

(10) Patent No.: US 7,769,215 B2
(45) Date of Patent: Aug. 3, 2010

(54) METHOD, SYSTEM, AND MEDIUM FOR PREVALENCE-BASED COMPUTERIZED ANALYSIS OF MEDICAL IMAGES AND INFORMATION

(75) Inventors: Karla Horsch, Lombard, IL (US); Maryellen L. Giger, Elmhurst, IL (US); Charles E. Metz, Burr Ridge, IL (US); Carl J. Vyborny, Riverside, IL (US); Terrieann Vyborny, legal representative, Riverside, IL (US); Li Lan, Naperville, IL (US)

(73) Assignee: The University of Chicago, Chicago, IL (US)

( * ) Notice: Subject to any disclaimer, the term of this patent is extended or adjusted under 35 U.S.C. 154(b) by 1287 days.

(21) Appl. No.: 10/997,935

(22) Filed: Nov. 29, 2004

(65) Prior Publication Data

US 2005/0234570 A1 Oct. 20, 2005

Related U.S. Application Data

(60) Provisional application No. 60/525,198, filed on Nov. 28, 2003.

(51) Int. Cl.
*G06K 9/00* (2006.01)

(52) U.S. Cl. ........................ 382/128; 382/130; 382/131

(58) Field of Classification Search ......... 382/128–134, 382/154, 173, 237; 600/408, 407, 425–429, 600/410, 454, 436, 437; 128/925, 922–923, 128/920; 700/93; 378/98.2, 98.8; 345/204, 345/419, 427; 356/12.37
See application file for complete search history.

(56) References Cited

U.S. PATENT DOCUMENTS 5,537,485 A * 7/1996 Nishikawa et al. .......... 382/130
5,836,872 A * 11/1998 Kenet et al. ................. 600/306
5,860,917 A * 1/1999 Comanor et al. ............ 600/300
6,058,322 A 5/2000 Nishikawa et al.
6,115,488 A * 9/2000 Rogers et al. ............... 382/132
6,738,499 B1 * 5/2004 Doi et al. .................... 382/128

* cited by examiner

*Primary Examiner*—Samir A. Ahmed
*Assistant Examiner*—Mehdi Rashidian
(74) *Attorney, Agent, or Firm*—Oblon, Spivak, McClelland, Maier & Neustadt, L.L.P.

(57) ABSTRACT

A method for computer-assisted interpretation of medical images that factor in characteristics of an individual performing the interpretation. The method automatically determines and/or incorporates prevalence-based computer analysis based on an estimated likelihood of a pathological state, e.g., a malignancy. A system implementing the method includes the calculation of features or other characteristics of images in a known database, calculation of features of an unknown case, calculation of the probability (or likelihood) of disease state, calculation of the modified computer output that includes the internal prevalence (or internal decision-making process) of the user (or group of users), and output of the result.

20 Claims, 15 Drawing Sheets

Medical Image or Information — 101
Computerized (Image) Analysis of Lesion — 102
Intermediate Computer output in terms of the Probability of Malignancy (PM) — 103
Desired Prevalence — 106
PM is modified by the Prevalence Modification Transformation — 105
Computer Output of Prevalence-Modified Probability of Malignancy — 107

METHOD, SYSTEM, AND MEDIUM FOR PREVALENCE-BASED COMPUTERIZED ANALYSIS OF MEDICAL IMAGES AND INFORMATION

CROSS-REFERENCE TO RELATED APPLICATIONS

This application claims the benefit under 35 U.S.C. §119 of the filing date of Provisional Application No. 60/525,198, filed Nov. 28, 2003, the contents of which are incorporated herein by reference.

BACKGROUND OF THE INVENTION

1. Field of the Invention

The present invention is related to the field of computer-assisted medical diagnosis and image display workstations. More precisely, the present invention is directed to computer-assisted medical diagnosis and image display systems utilizing estimates of a probability of malignancy (PM) of a lesion determined by training a classifier using empirical data.

The present invention includes the use of various technologies referenced and described in the documents identified in the following LIST OF REFERENCES, which are cited throughout the specification by the corresponding reference number in brackets:

LIST OF REFERENCES

[1] Huo Z, Giger M L, Vyborny C J, Bick U, Lu P, Wolverton D E, and Schmidt R A, Analysis of spiculation in the computerized classification of mammographic masses, *Medical Physics* 22:1569-1579, 1995.

[2] Huo Z, Giger M L, Vyborny C J, Wolverton D E, Schmidt R A, and Doi K, Automated computerized classification of malignant and benign mass lesions on digitized mammograms, *Academic Radiology* 5: 155-168, 1998.

[3] Huo Z, Giger M L, and Metz C E, Effect of dominant features on neural network performance in the classification of mammographic lesions, *PMB* 44: 2579-2595, 1999.

[4] Swett H A, Fisher P R, Cohn A I, Miller P L, and Mutalik P G, Expert system controlled image display, *Radiology* 172:487-493, 1989.

[5] Swett H A and Miller P A, ICON: a computer-based approach to differential diagnosis in radiology, *Radiology* 163:555-558, 1987.

[6] Sklansky J, Taso E Y, Ornes C, and Disher A C, A visualized mammographic database in computer-aided diagnosis, *Computer-Aided Diagnosis in Medical Imaging*, Eds. Doi K, MacMahon, Giger M L, and Hoffmann K R, pages 215-220, Elsevier Science, 1999.

[7] Giger M L, Huo Z, Kupinski M A, and Vyborny C J, Computer-aided diagnosis in mammography, In *Handbook of Medical Imaging, Volume* 2. *Medical Imaging Processing and Analysis*, (Sonka M, Fitzpatrick M J, eds.) SPIE, pages 915-1004, 2000.

[8] Gur D, From the Laboratory to the Clinic: The "Prevalence Effect", *Acad. Radiol.* 10:1324-1326, 2003.

[9] Van Trees H L, Detection, estimation and modulation theory (Part I), New York, Academic Press, 1968.

[10] Metz C E, Herman B A, and Shen J-H, Maximum-likelihood estimation of ROC curves from continuously-distributed data. *Stat. Med.* 17: 1033, 1998.

[11] Pan X and Metz C E, The "proper" binormal model: parametric ROC curve estimation with degenerate data, *Academic Radiol.* 4:380, 1997.

[12] Metz C E and Pan X, "Proper" binormal ROC curves: theory and maximum-likelihood estimation, *J Math. Psych.* 43:1, 1999.

[13] Horsch K, Giger M L, Vyborny C J, and Venta L A, Performance of CAD in the interpretation of lesions on breast sonography, *Acad. Rad.*, in press, 2004.

The entire contents of the contents of each reference listed in the LIST OF REFERENCES are incorporated herein by reference.

2. Discussion of the Background

Breast cancer causes an estimated 46,000 deaths per year and is a leading cause of death in women. The need for methods to effectively detect breast cancer in its early stages is therefore evident and urgent. Currently, mammography is the most effective such method and it has been shown that periodic screening of asymptomatic women does reduce mortality. However, more needs to be done.

Breast cancer is often detected and referred for surgical biopsy on the basis of a radiographically detected mass lesion or cluster of microcalcifications. There are general rules for differentiating between benign and malignant mammographically identified breast lesions. However, current methods yield considerable rates of misclassification among suspect lesions. In fact, fewer than 30% of masses referred for surgical breast biopsy are actually malignant, on average.

The probability of malignancy (or any other pathologic state) depends on the prevalence of the cancer (or other disease) in the population from which it was drawn. An estimate of the probability of malignancy obtained by a computer may be confusing to a radiologist because it reflects the computer's prevalence instead of the radiologist's. Thus, it is desirable to transform the computer's estimate for the PM to reflect the radiologist's internal prevalence.

Further, a differing prevalence may not be the only source of confusion to the radiologist. A general monotonic transformation of the computer's estimate for the PM to reflect the radiologist's internal decision-making processes relative to the computer may be what is needed. However, it is important to note that the transformation of the computer probability of malignancy should not change the performance of the computer classifier in the task of distinguishing diseased from non-diseased states. Prevalence modification is one example of a transformation that has no effect on performance.

Whereas methods of computer detection and diagnosis of lesions have been developed, useful interfaces for communicating an output of a computer to a user are inadequate because the computer output fails to account for the human perceived estimation of cancer prevalence in their practice. That is, the computer output fails to match the types and number of cases seen in a specific radiologist practice.

Intelligent workstations and/or computer output that aid radiologists in diagnosing cancer promise to reduce the biopsy rate of benign lesions while maintaining high sensitivity. Such methods/workstations utilize an estimate of a lesion's probability of malignancy, usually by training a classifier on an independent database.

Estimates of the probability of malignancy are dependent on the prevalence of cancer in the independent database, which most often does not correspond to the prevalence of cancer in the population from which the user has experience, e.g., the population seen in the user's medical practice. Thus, the user often has difficulty interpreting the computer-estimated probability of malignancy.

The potential usefulness of computer-aided diagnosis as an aid to radiologists in the characterization and classification of mass lesions in mammography has been investigated. Studies have shown that such a system can aid in increasing the diagnostic accuracy of radiologists both in terms of sensitivity and specificity.

An intelligent search display incorporating the computerized mass classification method was also developed. Upon viewing an unknown mammographic case, the display shows both the computer classification output as well as images of lesions with known diagnoses (e.g., malignant vs. benign) and similar computer-extracted features.

The similarity index used in the search can be chosen by the radiologist to be based on a single feature, multiple features, or on the computer estimate of the likelihood of malignancy [7]. The output of a computer-assisted diagnostic scheme can take a variety of forms such as the estimated likelihood that a lesion is malignant either in terms of probabilities or along a standardized rating scale. This information is then available for use by the radiologist as he or she sees fit when making decisions regarding patient management.

An alternative approach is for the computer to display a variety of lesions that have characteristics similar to the one at hand and for which the diagnosis is known, thereby providing a visual aid for the radiologist in decision making. An early workstation recalls lesions in the known database based either on a single feature, multiple features, or computer-estimate of the likelihood of malignancy. In addition, instead of just displaying typical malignant and benign cases that are similar, the computer display shows relative similarity of the malignant and benign known cases by use of a color-coding of the similar lesions. Basically, the probability distributions of the malignant and benign cases in the known database are shown by images along with the "location" of the unknown case relative to the two distributions.

The intelligent search workstation combines the benefit of computer-assisted diagnosis with prior knowledge obtained via confirmed cases. It is expected that the display of known lesions with similar features will aid the radiologist in his/her workup of a suspect lesion, especially when the radiologist's assessment of the lesion differs from the computer output [7].

However, such methods/workstations utilize an estimate of a lesion's probability of malignancy usually obtained by training a classifier on an independent database. These estimates of the probability of malignancy are dependent on the prevalence of cancer in the independent database, which most often does not correspond to the prevalence of cancer in the population from which the user has experience, e.g., the population seen in the user's medical practice. Different prevalences may affect the interpretation abilities of radiologists [8]. Thus, the user often has difficulty interpreting the computer-estimated probability of malignancy.

SUMMARY OF THE INVENTION

Accordingly, an object of the present invention is to provide a method and system employing either computer analysis or an intelligent workstation for computer-assisted interpretation of medical images.

Another object of the present invention is to provide a method for determining the internal prevalence (characteristics) of an individual or a group of readers.

Another object of the present invention is to provide a method of modifying a computer-estimated probability of a disease state to reflect that of the interpreter (e.g., a radiologist or practice of radiologists).

Another object of the present invention is to provide an automated method and system employing/incorporating prevalence-based computer analysis for computer-assisted interpretation of medical images based on a computer-estimated likelihood of a pathological state, e.g., malignancy.

Another object of the present invention is to provide a method and system employing an intelligent workstation for computer-assisted interpretation of medical images to provide the radiologist/physician with output from the computer analysis of the medical images, which output has been modified by the known prevalence of cancer within a radiologists experience/mental assessment or within a practice of a group of radiologists, etc.

These and other objects are achieved according to embodiments of the present invention by providing a new automated method and system employing an intelligent prevalence-based computer system/workstation for computer-assisted interpretation of medical images.

Accordingly, an object of the present invention is to provide a method for determining a probability of a disease state for a patient, comprising: (1) obtaining medical information, including at least one of a medical image, information representative of the medical image, and information representative of a clinical examination of the patient; (2) calculating the probability of the disease state based on the obtained medical data; (3) transforming the calculated probability using an input calibration factor based on the disease state; and (4) outputting the transformed probability of the disease state.

In addition, there is provided a method, system, and computer program product for determining an internal calibration factor of a classifier, comprising: (1) obtaining medical information including at least one of medical image data and information representative of the medical image data; (2) obtaining at least one probability of a diseased state calculated by the classifier based on the obtained medical image information; and (3) determining the internal calibration factor of the classifier based on the obtained at least one probability.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
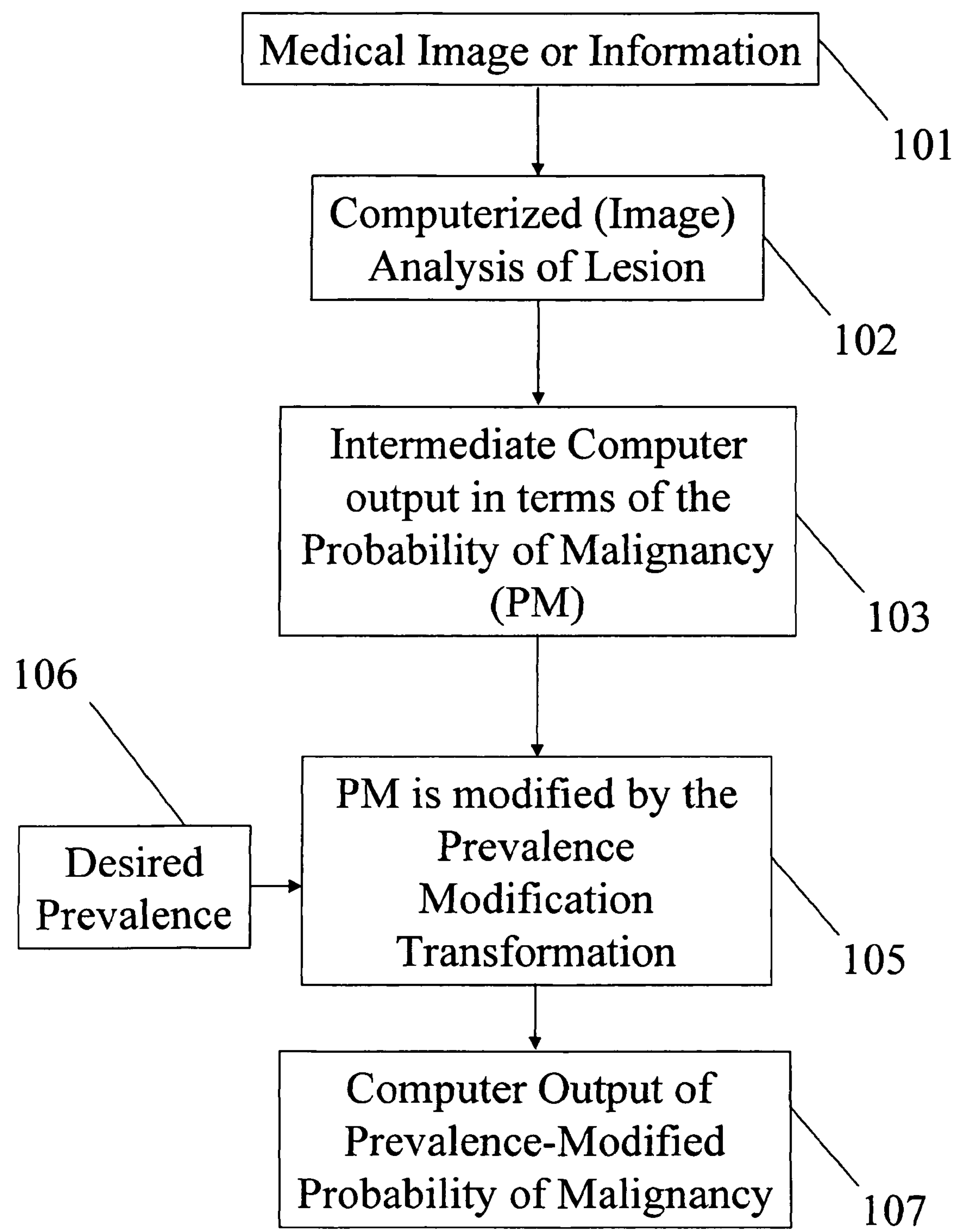
FIG. 1 illustrates a method for incorporating prevalence-modified probabilities into computer-assisted interpretation of medical images.

Embodiments of the present invention describe methods and systems for estimating the prevalence of an individual or a group or for estimating a monotonic transformation modeling the internal decision-making processes relative to the computer of an individual or a group and for incorporating such estimates into the computerized analysis for computer-assisted interpretation of medical images and/or information based on computer-estimated likelihood of a pathological state, e.g., malignancy.

Upon viewing an unknown medical case, the computer outputs an analysis expressed either in terms of characteristics of the individual performing the interpretation, in terms of the characteristics of the particular group (or practice) of interpreters (i.e., the radiologists), or in terms of any other group or individual given that the characteristics (prevalence or internal decision-making transformation) of that group is known.

According to an embodiment of the present invention, an automated method and a system implementing this method determine and/or employ/incorporate prevalence-based computerized analysis for computer-assisted interpretation of medical images based on computer-estimated likelihood of a pathological state, e.g., malignancy.

According to an embodiment of the present invention, an intelligent computer output/workstation utilizes prevalence-modified estimates of a lesion's probability of malignancy. This can include a method for determining the transformation and implementing computer-estimated probabilities of malignancies to those representative of a database with a known prevalence of cancer.

According to an embodiment of the present invention, an intelligent workstation/interface/method utilizes prevalence-modified estimates of a lesion's probability of malignancy. This can include a method for determining the internal prevalence and a method for the transformation of computer-estimated probabilities of malignancies to be more representative of a database/practice/radiologist with a known prevalence of cancer.

According to an embodiment of the present invention, an automated method and a system employ/incorporate prevalence-based computerized analysis for computer-assisted interpretation of medical images based on computer-estimated likelihood of a pathological state, e.g., malignancy.

The overall method includes an initial acquisition of a set of known medical images that comprise a database, and presentation of the images in digital format. The lesion location in terms of estimated center is input from either a human or computer. The method and system that employs an intelligent workstation for the computer assisted interpretation of medical images includes: access to a database of known medical images with known/confirmed diagnoses of pathological state, computer-extraction of features of lesions within the known database, input method for an unknown case, computer-extraction of features of lesion of the unknown case, calculation of modified computer output utilizing the prevalence of the radiologist, and output including, for example, presentation of "similar" cases and/or the computer-estimated features and/or likelihood of pathological state.

FIG. 1 illustrates schematically a method employing/incorporating prevalence-modified probabilities of being in a disease state (e.g., probability of malignancy) into a computerized image analysis output/workstation for computer-assisted interpretation of medical images. In the exemplary embodiment of FIG. 1, a medical image or related information mass lesions is obtained in step 101, mammographic and sonographic images, for example. In step 102, a computer extracts features of the images, and in step 103, the computer estimates the likelihood of malignancy for the known and the unknown cases. According to a desired prevalence prescribed in step 106, an estimate of the internal prevalence of the user is modified using the determined internal prevalence in step 105. Finally, a computer output of the prevalence-modified probability of malignancy is provided in step 107.

Figure 2:
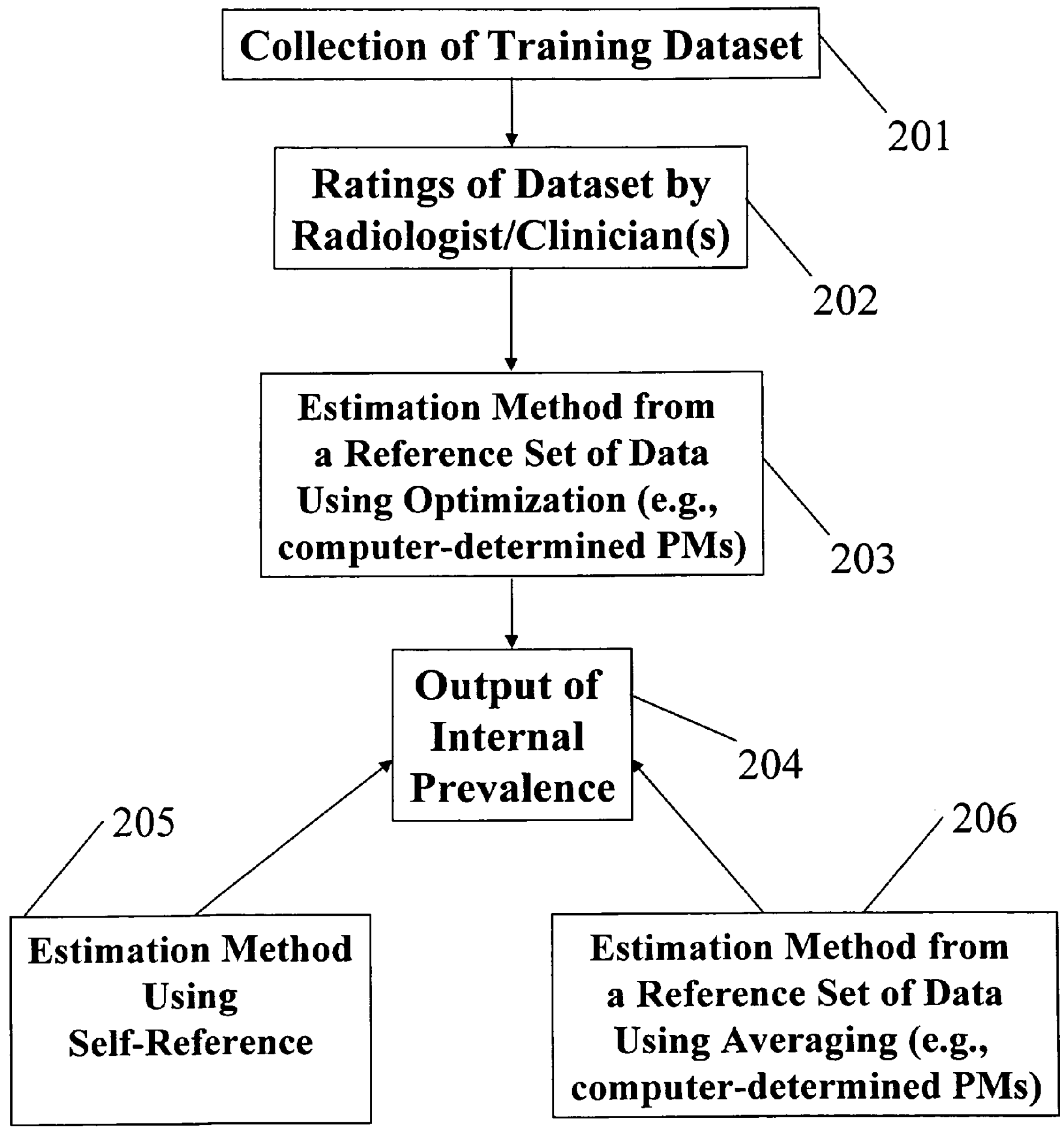
FIG. 2 illustrates a method for determining the internal prevalence for a radiology practice.

FIG. 2 illustrates schematically a method for determining the internal prevalence of a radiologist (or a practice/group of radiologists). In step 201, a collection of training data is obtained. In step 202, a radiologist, clinician, or group of radiologists and/or clinicians provide ratings for the training data elements. In steps 203, 205, and 206, respectively, an estimation method based on optimization, self-reference, and averaging is used to estimate the internal prevalence which is outputted in step 205.

Figure 3:
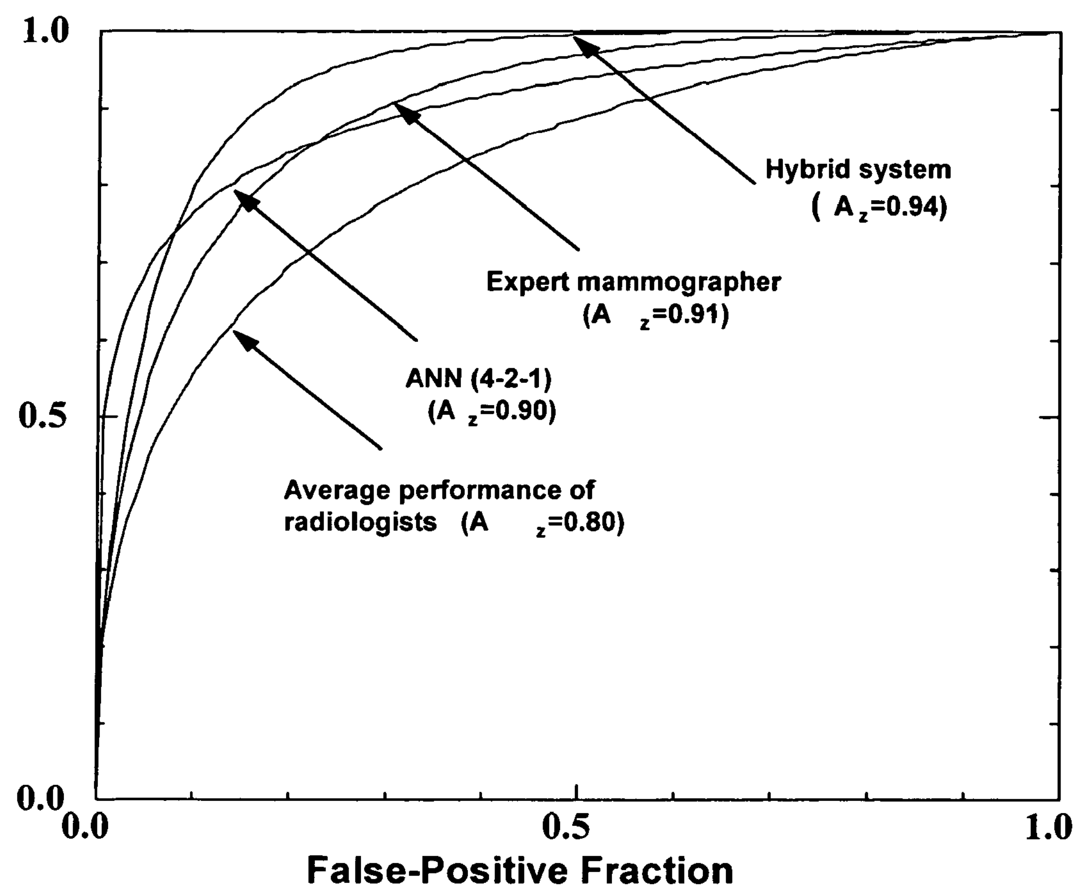
FIG. 3 illustrates receiver operating characteristic (ROC) curves associated with various performances at distinguishing between benign and malignant lesions.

FIG. 3 illustrates the performance in terms of ROC curves of the computer analysis on the database used as the reference database in the intelligent search workstation.

The performance is given for the task of distinguishing malignant from benign lesions. The images in this study were either obtained by mammography followed by film digitization or obtained directly from the ultrasound system. The database used in this study consisted of clinical mammograms (Kodak MinR screen/OM-1 film, Eastman Kodak, Rochester, N.Y.), each containing a mass. The computerized mass classification method was independently evaluated on a 110-case clinical database consisting of 50 malignant and 60 benign cases.

According to embodiments of the present invention, a method for automated classification of mass lesions comprises: (1) automated segmentation of mass regions, (2) automated feature-extraction, and (3) automated classification [1,2].

The segmentation of a mass from the background parenchyma can be accomplished using a multiple-transition-point, gray-level region-growing technique. Segmentation begins within a 512 by 512 pixels region of interest manually centered about the abnormality in question.

In clinical practice, the location of the mass could be identified either by a radiologist or by a computer-detection scheme and then fed into the classification scheme for an output on the likelihood of malignancy. In order to correct for the non-uniformity of the background distribution and to enhance image contrast for better segmentation of masses, background trend correction and histogram equalization techniques are applied to the 512 by 512 pixels region of interest.

The margin, shape, and density of a mass are three major mammographic characteristics used by radiologists in classifying masses. Different characteristics of these features are associated with different levels of probabilities of malignancy. In order to determine the likelihood of malignancy associated with different margin and density characteristics, algorithms extracting two features that characterize the margin of a mass (spiculation and sharpness) and three features that characterize the density of a mass (average gray-level, contrast and texture) were developed.

Margin characteristics are very important discriminants in differentiating between benign and malignant masses. In order to determine the likelihood of malignancy of a mass based on its margin, two major margin characteristics—a spiculation measure and a margin-sharpness measure—are used. Margin spiculation is the most important indicator for malignancy, with spiculated lesions having a greater than 90% probability of malignancy. Margin sharpness is also very important in the determination of the benign vs. malignant nature of a mass—with an ill-defined margin indicating possible malignancy and a well-defined margin indicating likely benignity. Only about 2% of well-defined masses are malignant.

The spiculation measure is obtained from an analysis of radial edge gradients. The spiculation measure evaluates the average angle (degrees) by which the direction of the maximum gradient at each point along the margin of a mass deviates from the radial direction, the direction pointing from the geometric center of the mass to the point on the margin.

The actual measure is the FWHM (full width at half-maximum) of the normalized edge-gradient distribution calculated for a neighborhood of the grown region of the mass with respect to the radial direction. This measure is able to quantify the degree of spiculation of a mass primarily because the direction of maximum gradient along the margin of a spiculated mass varies greatly from its radial direction, whereas the direction of the maximum gradient along the margin of a smooth mass is similar to its radial direction.

The spiculation measure achieved a similar level of performance ($A_Z$=0.88) to that of the experienced mammographer's spiculation ratings ($A_Z$=0.85) in terms of the ability to distinguish between benign and malignant masses based solely on spiculation [1].

The sharpness of the margin of a mass can be described as well-defined, partially ill-defined, or ill-defined. The average margin sharpness can be quantified by calculating the magnitude of the average gradient along the margin of the mass. A well-defined margin has a large value for the average margin sharpness measure, whereas an ill-defined margin has a small value.

Although the radiographic density of a mass may not be by itself as powerful a predictor in distinguishing between benign and malignant masses as its margin features, taken with these features, density assessment can be extremely useful. The evaluation of the density of a mass is of particular importance in diagnosing circumscribed, lobulated, indistinct, or obscured masses that are not spiculated.

In order to assess the density of a mass radiographically, three density-related measures (average gray level, contrast, and texture measure) that characterize different aspects of the density of a mass are used. These measures are similar to those used intuitively by radiologists.

Average gray level is obtained by averaging the gray level values of each point within the grown region of a mass. Contrast is the difference between the average gray level of the grown mass and the average gray level of the surrounding fatty areas (areas with gray-level values in the lower 20% of the histogram for the total surrounding area). Texture is defined here as the standard deviation of the average gradient within a mass and it is used to quantify patterns arising from veins, trabeculae, and other structures that may be visible through a low-density mass, but not through a high-density mass.

A mass of low radiographic density should have low values of average gray level and contrast, and a high value of the texture measure, whereas a mass of high radiographic density should have high values of average gray level and contrast, and a low value of the texture measure.

For sonographic CAD, the computer calculates four features related to the lesion's shape, margin, texture, and posterior acoustic behavior. Lesion shape is characterized by a depth-to-width ratio and lesion margin is characterized by the normalized radial gradient (which yields the average orientation of the gray level gradients along the margin).

Lesion texture is characterized by an autocorrelation function and the posterior acoustic behavior is characterized by comparing the gray-level values posterior to the lesion to those in adjacent tissue at the same depth [13].

In embodiments of the present inventions, three automated classifiers were investigated for the task of merging the computer-extracted features into an estimate of the likelihood of malignancy: (1) a rule-based method; (2) an artificial neural network (ANN); and (3) a hybrid system (i.e., combination of a one-step rule-based method and an artificial neural network).

In determining the likelihood of malignancy for the cases that had both the medio-lateral-oblique and cranio-caudal views, the measurements obtained from both views were considered and the one with the higher likelihood of malignancy estimated by the computer was used in the evaluation.

For example, in these cases, a mass would be classified as malignant if either one of the two views showed suspicious signs, i.e., either one of the FWHM measures from its two views satisfied the cutoff on the FWHM measure.

A rule-based method adopts knowledge from experts into a set of simple rules. Certain criteria for differentiating between benign and malignant masses have been established by expert mammographers. The rules employed here for spiculation, margin-sharpness and density measures were based on these criteria. A two-step rule-based method was studied for this database. Because of its clinical diagnostic significance, the spiculation measure was applied first in the rule-based method. After the spiculation measure (FWHM) was applied to identify spiculated masses (including some irregular masses) and categorized them as malignant first, a second feature was applied to further characterize the masses in the non-spiculated category as previously discussed.

In order to investigate the potential discriminant ability of the spiculation measure along with all the possible secondary features, each of the remaining four features—the margin-sharpness measure and the three density measures—can be applied separately after the spiculation measure. The threshold of the spiculation measure (FWHM of 160 degrees) was determined based on the entire database. The thresholds of the other four features were determined based on the remaining database only.

The ANN approach is quite different from the rule-based method. Instead of using pre-specified empirical algorithms based on prior knowledge, ANNs are able to learn from examples and therefore can acquire their own knowledge through learning. Also, neural networks are capable of processing large amounts of information simultaneously. Neural networks do not, however, provide the user with explanations about their decisions and may not be able to bring pre-existing knowledge into the network. A conventional three-layer, feed-forward neural network with a back-propagation algorithm, which has been used in medical imaging and medical decision making, can be used. The structure of the neural network included four input units (each of which corresponded to a computer-extracted feature), two hidden units, and one output unit.

To determine the ability of such a neural network to generalize from the training cases and make diagnoses for cases that had not been included in the database, a round-robin method also known as the leave-one-out method can be used. In this method, all but one case were used to train the neural network. The single case that was left out was used to test the neural network.

For the cases having both medio-lateral-oblique and cranio-caudal views, both images of the pair were left out in the round-robin training. The higher value of the two from the round-robin test was reported as the estimated likelihood of malignancy. This procedure was repeated for all the cases.

Each classifier has its advantages and limitations. With rule-based methods, one could adopt pre-existing knowledge as rules. However, there are limitations in the availability of knowledge and knowledge translation. Even the experts find it difficult to articulate particular types of "intuitive" knowledge, and the process of translating particular knowledge into rules is limited by this expressive power.

ANNs are capable of learning from examples and therefore can acquire their own knowledge. It may be most advantageous to use ANNs when intuitive knowledge cannot be explicitly expressed or is difficult to translate. However, the ANN requires a sufficiently large database to learn effectively.

Also, with an ANN there may be uncertainty as to whether the final learning goal is achieved in some situations. To take advantage of both rule-based systems and ANNs in the task of classifying masses, a rule-based method and an ANN were integrated into a hybrid system wherein a rule is initially applied on the spiculation measure since both spiculated and irregular masses are highly suspicious for malignancy, and an ANN is then applied to the remaining masses. Basically, this frees the ANN from having to "learn" the significance of spiculation to the detriment of learning the significance of the other features.

The threshold of the spiculation measure for the hybrid system was the same as the one used in the rule-based method. The ANN applied in the hybrid system was a three-layer, feed-forward neural network with a back-propagation algorithm that had a structure of three input units (corresponding to the three remaining features used in the ANN method), two hidden units, and one output unit. The same round-robin method was applied to test the generalization ability of such a neural network to differentiate between benign and malignant masses in the non-spiculated category.

In an exemplary embodiment of the invention, the method was initially trained with 95 mammograms containing masses from 65 patients. Features related to the margin, shape, and density of each mass are extracted automatically from the image data and merged into an estimate of the likelihood of malignancy using artificial neural networks. These features include a spiculation measure, a radial gradient index, and two density measures. The round-robin performance of the computer in distinguishing between benign and malignant masses was evaluated by receiver operating characteristic (ROC) analysis.

The computer classification scheme yielded an $A_Z$ value of 0.94, similar to that of an experienced mammographer ($A_Z$=0.91) and statistically significantly higher than the average performance of five radiologists with less mammographic experience ($A_Z$=0.81). With the database used, the computer scheme achieved, at 100% sensitivity, a positive predictive value of 83%, which was 12% higher than that of the experienced mammographer and 21% higher than that of the average performance of the less experienced mammographers at a p-value of less than 0.001.

The computerized mass classification method was independently evaluated on a 110-case clinical database consisting of 50 malignant and 60 benign cases. The effects of variations in both case mix and in film digitization technique on the performance of the method were assessed. Categorization of lesions as malignant or benign using the computer achieved an $A_Z$ value (area under the ROC curve) of 0.90 on the prior training database (Fuji scanner digitization) in a round-robin evaluation, and $A_Z$ values of 0.82 and 0.81 on the independent database for Konica and Lumisys digitization formats, respectively. However, in the statistical comparison of these performances, we failed to show a statistical significant difference between the performance on the training database and that on the independent validation database (p-values>0.10). Thus, such a computer-based method for the classification of lesions on mammograms was shown to be robust to variations in case mix and film digitization technique.

Every diagnostic classifier, whether human or computer, is trained on some population. The training population for a radiologist, or human classifier, is the population of the radiologist's experience. The training population for the computer is the population upon which the computer classifier was trained. A classifier's estimate of the probability of malignancy for a particular case is dependent on the prevalence of cancer in the training population, or the "training prevalence" (or "internal prevalence").

Intelligent computer systems/workstations that assist radiologists in diagnosing cancer promise to reduce the biopsy rate of benign lesions while maintaining high sensitivity. Such workstations utilize an estimate of a lesion's probability of malignancy (PM), usually by training a classifier on an independent database. These estimates of the PM are dependent on the prevalence of cancer in the independent database, which most often does not correspond to the prevalence of cancer in the population from which the user has experience, e.g., the population seen in the user's medical practice. To alleviate the difficulty the user may have in interpreting the computer-estimated probability of malignancy, computer systems/intelligent workstations utilizing prevalence-modified estimates of a lesion's PM are developed.

The prevalence-modified estimate of the probability of malignancy can be computed using Bayes' rule [9] which relates the probability of malignancy to the training database prevalence and the likelihood ratio. The usefulness of prevalence-modified probabilities of malignancy obtained using classifiers trained on databases with various prevalences and transformed to represent databases with other prevalences has been investigated. For example, a database with a prevalence of 0.5, i.e., 50% cancer, 50% non-cancer, yields specific computer-estimated probabilities of malignancy. These can be modified once the prevalence in which a given radiologists works is known. If the radiologist works in a practice with a 0.20 prevalence of breast cancer during the workup stage, then the computer outputs can be modified to reflect that prevalence.

An estimate of the prevalence best suited to the user can be used to transform the computer-estimated PM into a prevalence-modified estimate of the PM. Bayes' rule yields for the computer-estimated PM given a feature vector x, an equation in terms of the training database prevalence η and the likelihood ratio R(x)

$$P(\pi_m \mid x) = \frac{\eta R(x)}{\eta R(x) + 1 - \eta}.$$

Here, π is a discrete variable that may take on one of two values: $\pi_m$ (malignant) and $\pi_b$ (benign). Solving for R yields $$R(x) = \frac{(1-\eta)P(\pi_m \mid x)}{\eta(1 - P(\pi_m \mid x))}. \tag{1}$$

Therefore, the prevalence-modified estimate of the PM can be computed by $$P'(\pi_m \mid x) = \frac{\eta' R(x)}{\eta' R(x) + 1 - \eta'} \tag{2}$$

where η' is an estimate of the modified prevalence, that is, the prevalence best suited to the user.

Figure 4:
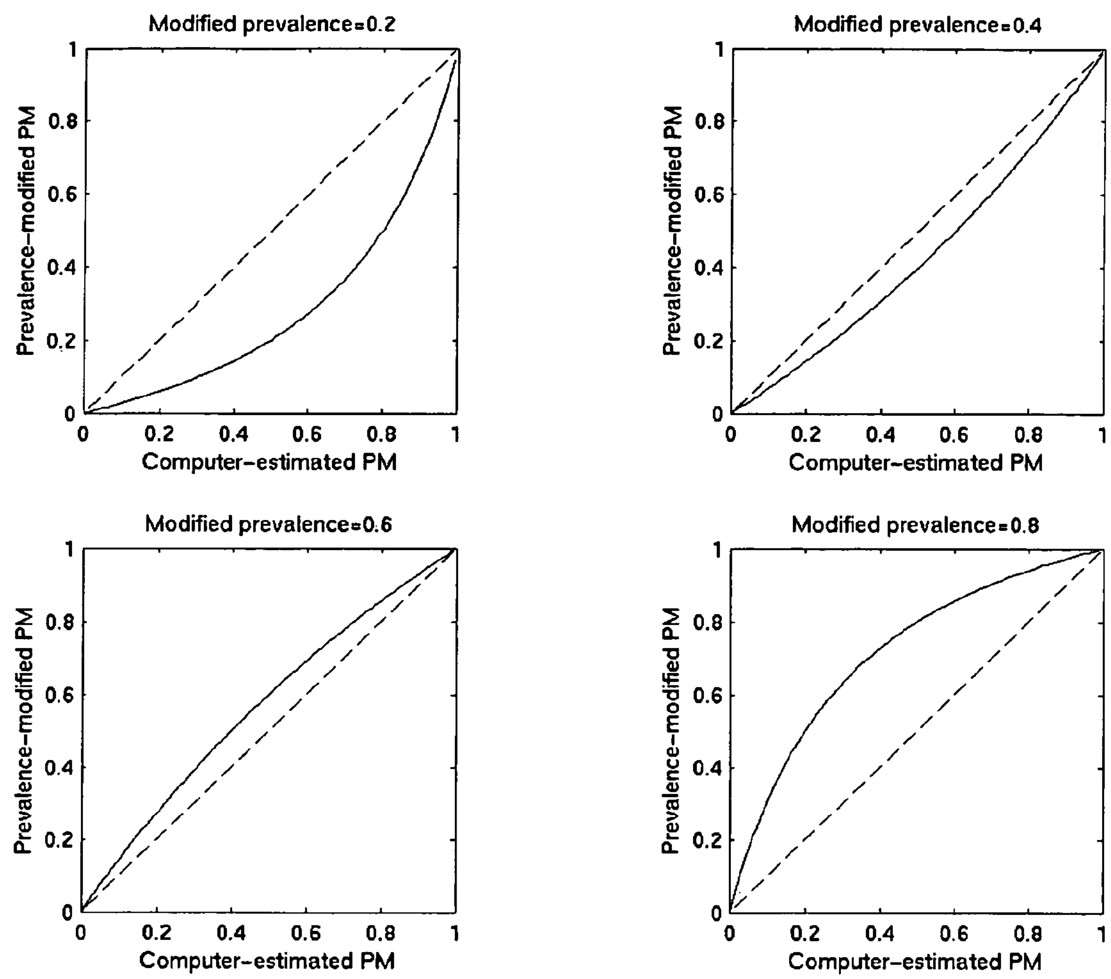
FIG. 4 illustrates prevalence-modified probabilities of malignancy for various values of modified prevalence.

FIG. 4 illustrates the prevalence-modified estimate of the PM as a function of the computer-estimated PM for various values of modified prevalence. In this case, the classifier was trained on a database with a prevalence of 0.5, i.e., 50% cancer, 50% non-cancer.

Figure 5:
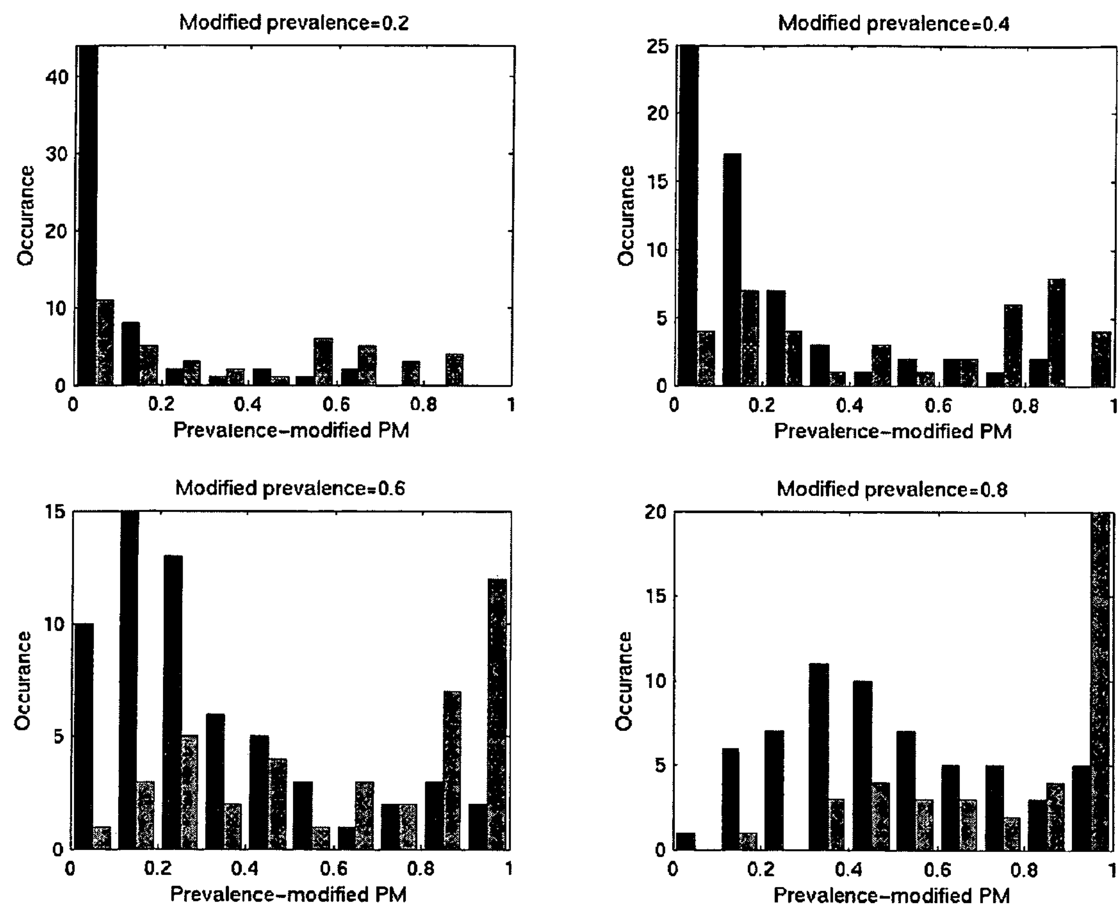
FIG. 5 illustrates histograms of the probability of malignancy for various values of modified prevalence.

An intelligent workstation may display a histogram of the probability of malignancy for the malignant and benign cases in the training database. FIG. 5 illustrates histograms of the probability of malignancy corresponding to modified prevalences of 0.2, 0.4, 0.6, and 0.8 for a mammographic database with prevalence 0.5.

An embodiment of the present invention includes an automated method and system that employs/incorporates prevalence-based computerized analysis for computer-assisted interpretation of medical images based on a computer-estimated likelihood of a pathological state, e.g., malignancy.

In such a workstation, the prevalence can be obtained by asking the user to input the prevalence of the population from which the user has experience. This method is simple, but problematic, as radiologists often do not know this information. Alternatively, the user is asked to define a PM for each case in a training database and these values of the PM are used to estimate the modified prevalence.

Figure 6:
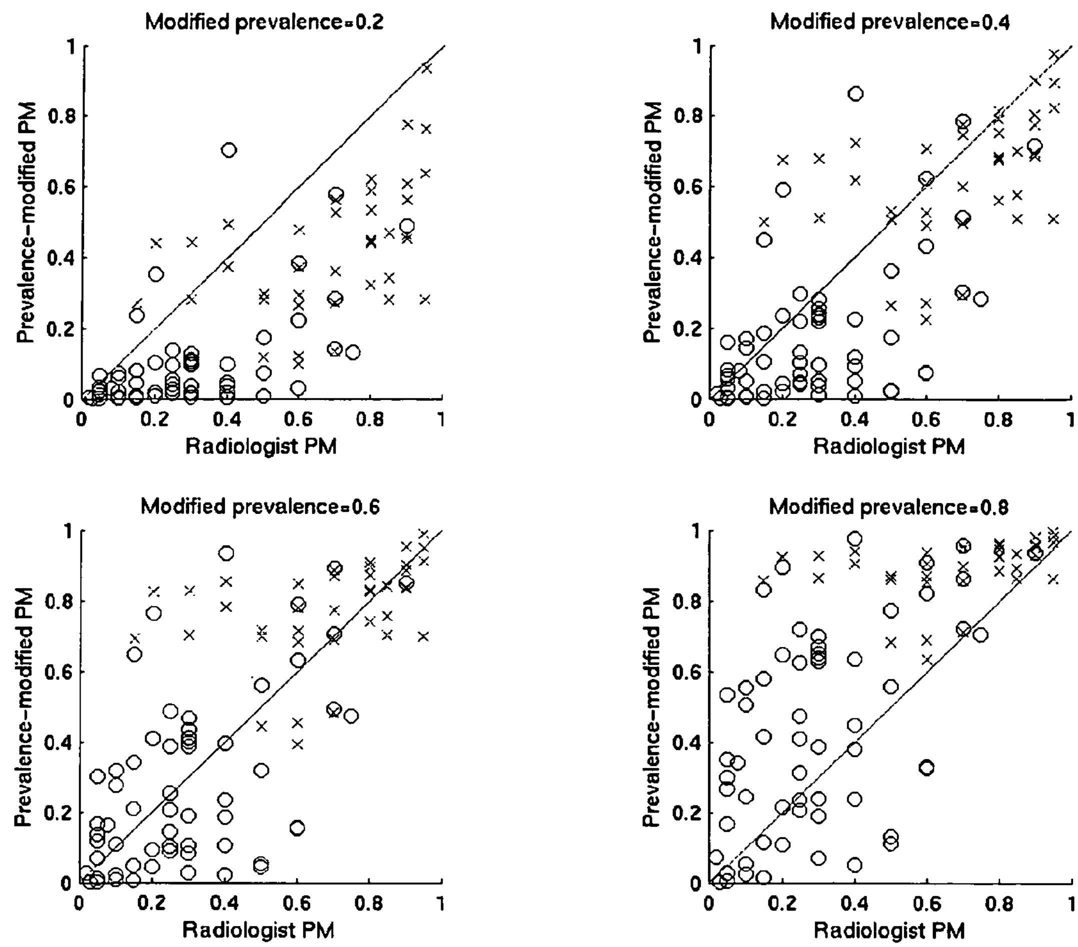
FIG. 6 illustrates the prevalence-modified and radiologist probabilities of malignancy for 100 ultrasound-detected breast lesions and various modified prevalences.

FIG. 6 illustrates the prevalence-modified PM as a function of radiologist PM for 100 cases of ultrasound-detected breast lesions, of which 40 were malignant and 60 were benign. The malignant lesions are represented by x and the benign lesions by o. In this case, the computer-estimated PM derives from a classifier that was trained on a sonographic database with prevalence 0.2.

Figure 7:
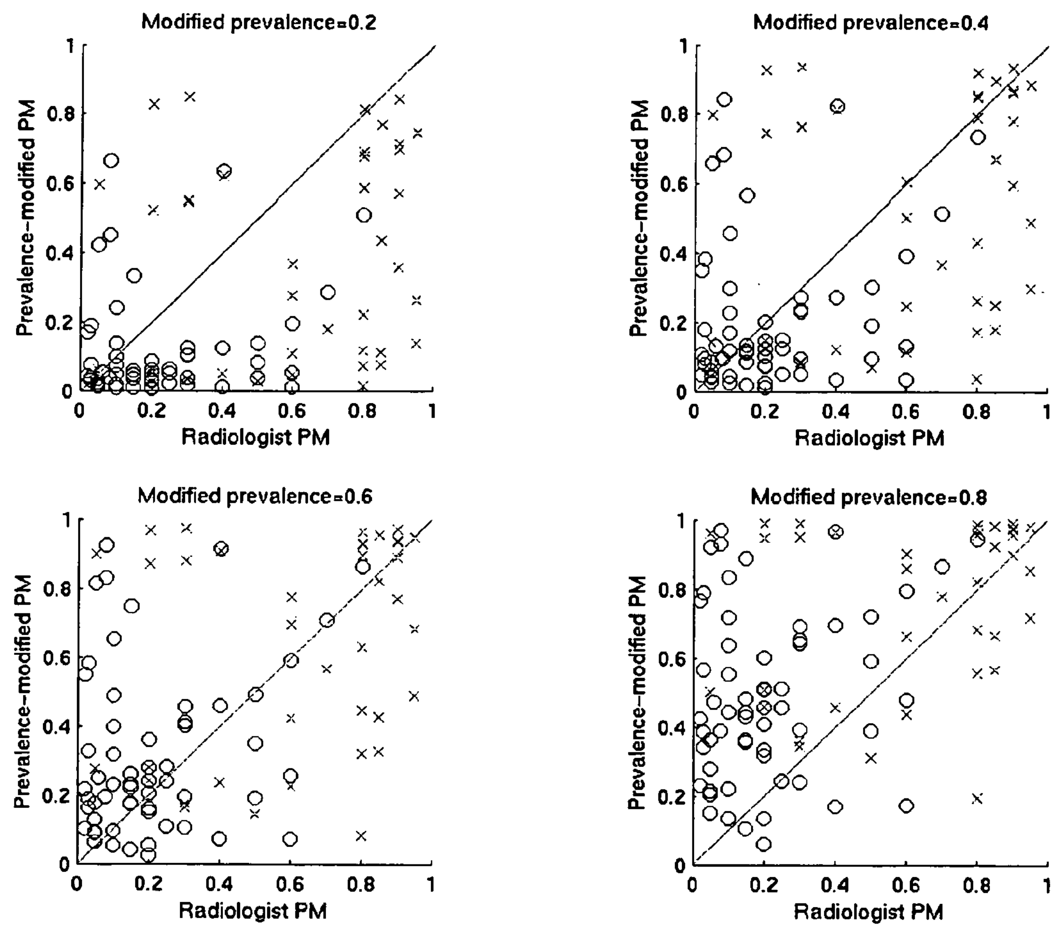
FIG. 7 illustrates the prevalence-modified and radiologist probabilities of malignancy for 100 mammography-detected breast lesions and various modified prevalences.

FIG. 7 illustrates the prevalence-modified PM as a function of radiologist PM for 100 cases of mammography-detected breast lesions, of which 40 were malignant and 60 were benign. The malignant lesions are represented by x and the benign lesions by o. In this case, the computer-estimated PM derives from a classifier that was trained on a mammographic database with prevalence 0.5.

To estimate the internal prevalence or "thought processes" of a particular classifier, either human or machine, one may use a classifier's estimates of the probability of malignancy on N cases, $\{y_i|i=1, 2, \ldots, N\}$. Here, the classifier can be human or machine.

Estimation using self-reference. Bayes' rule determines the PM given a feature vector x as a function of the prevalence η and the likelihood ratio R(x):

$$p(\pi_M \mid x; \eta) = B(\eta, R(x)) = \frac{\eta R(x)}{\eta R(x) + 1 - \eta}. \tag{1}$$

Here, π is a discrete variable that may take on one of two values: $\pi_m$ (malignant) and $\pi_b$ (benign). The likelihood ratio is defined by $$R(x) = \frac{p(x \mid \pi_m)}{p(x \mid \pi_b)}, \tag{2}$$

where the conditional density functions of the feature vector x are given by $p(x|\pi_m)$ for the malignant class and by $p(x|\pi_b)$ for the benign class.

Using estimates of the likelihood ratio at each of the N cases, $\{R(x_i)|i=1, 2, \ldots, N\}$, one may choose the prevalence η so that $\{B(\eta, R(x_i))|i=1, 2, \ldots, N\}$ best fits the classifier's estimate of the probability of malignancy $\{y_i i=1, 2, \ldots, N\}$.

For example, the following least squares fit estimates the training prevalence η by solving the minimization problem:

$$\min_{\eta} \sum_i (y_i - B(\eta, R(x_i)))^2.$$

One way to estimate the likelihood ratio at each of the N cases, is to estimate the conditional density functions of the feature vector x. This can be done by assuming that the $\{y_i|i=1, 2, \ldots, N\}$ follow normal distributions after some unknown monotonic transformation and performing maximum likelihood estimation on the resulting binormal ROC curve and its associated parameters [10].

The program LABROC4 [10] can perform this analysis and can be used to obtain the conditional density functions. Alternatively, the likelihood ratio may be directly estimated [11, 12]. Note that the program PROPROC [11, 12] estimates the likelihood ratio assuming a "proper" binormal model.

Table 1 provides the estimated internal prevalence for the computer and three radiologists using this method. The first row gives the prevalence estimates determined from the classifier's (human or machine) estimates of the probability of malignancy for 97 mammographic cases. The second row gives the prevalence estimates determined from the classifier's (human or machine) estimates of the probability of malignancy for 97 sonographic cases.

The computer classifiers are Bayesian neural nets, so that the computer's probability of malignancy automatically reflects the prevalence in the training databases. For mammography, the training databases prevalence was 0.55 and for sonography, it was 0.19. Note that the estimated prevalence for the computer agrees with actual prevalence in the training databases. Note further that for a given radiologist, there is a consistency across modalities in the estimated prevalence.

TABLE 1

| Estimated Prevalence | Computer | Radiologist 1 | Radiologist 2 | Radiologist 3 |
|---|---|---|---|---|
| Mammography | 0.55<br>Actual: 0.55 | 0.23 | 0.66 | 0.53 |
| Sonography | 0.19<br>Actual: 0.19 | 0.28 | 0.67 | 0.67 |

In this first estimation method, only the radiologist's estimation of the PM for N cases is used when the classifier is a radiologist, so that the method is independent of the computer's estimates of the PM.

Estimation from a reference set of data with known prevalence using optimization. If one has a second classifier's estimates of the probability of malignancy on the same N cases, $\{y_i|i=1, 2, \ldots, N\}$, and if the training prevalence η' for these estimates is known, then this information can be used to estimate the training prevalence η on the first classifier's estimates $\{y_i=1, 2, \ldots, N\}$.

One may derive a relation between the probability of malignancy with prevalence η and the corresponding probability of malignancy with prevalence η'. Solving for R(x) in equation (1) yields $$R(x) = \frac{(1-\eta)p(\pi_M \mid x; \eta)}{\eta(1-p(\pi_M \mid x; \eta))}. \tag{3}$$

Since the likelihood ratio is independent of prevalence, equation (3) may be substituted into the equation relating the PM given a feature vector x to the prevalence η':

$$p(\pi_M \mid x, \eta') = \frac{\eta' R(x)}{\eta' R(x) + 1 - \eta'}. \tag{4}$$

This substitution yields a transformation relating the PM at prevalence η' and the PM at prevalence η:

$$\begin{aligned} p(\pi_M \mid x; \eta) &= C(\kappa(\eta, \eta'), p(\pi_M \mid x; \eta')) \\ &= \frac{\kappa(\eta, \eta')p(\pi_M \mid x, \eta')}{\kappa(\eta, \eta')p(\pi_M \mid x, \eta') + 1 - \kappa(\eta, \eta')} \end{aligned}$$

$$\text{where } \kappa(\eta, \eta') = \frac{\eta(1-\eta')}{\eta'(1-\eta)}.$$

The prevalence η such that the transformed PM for the second classifier, $\{C(\kappa(\eta,\eta'), y_i')|i=1, 2, \ldots N\}$, best fits the PM for the first classifier can be found using an optimization algorithm. For example, a least squares estimation of the training prevalence η results from solving the minimization problem:

$$\min_{\eta} \sum_i (y_i - C(\kappa(\eta, \eta'), y_i'))^2.$$

Figure 8:
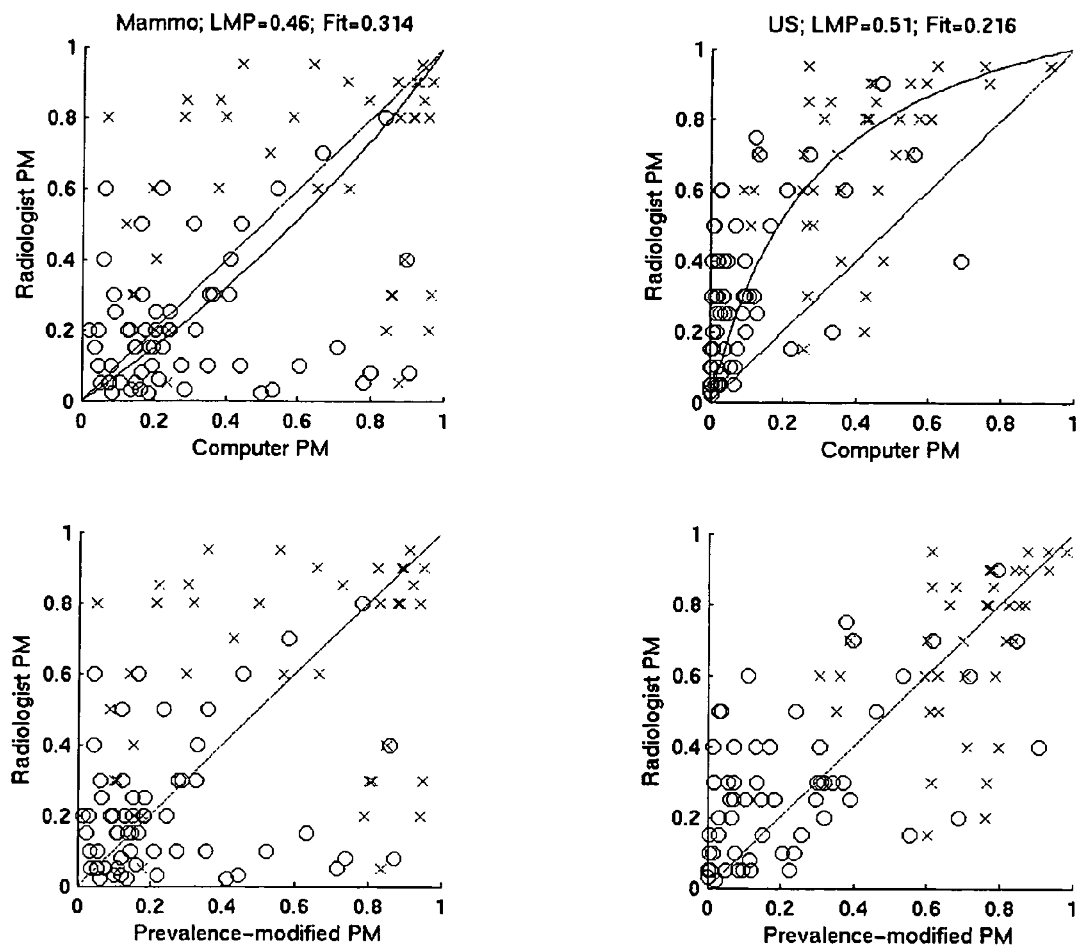
FIG. 8 illustrates least-square estimates of the relationship between the radiologist probability of malignancy and either the computer or the prevalence-modified probability of malignancy.

FIG. 8 illustrates exemplary estimates of the radiologist's prevalence obtained by the least square fitting technique for the training database (k=0.55 for mammography and k=0.19 for sonography). Upper curves compare the radiologist PM to the computer output PM. Lower curves relate the radiologist PM to the prevalence-modified PM.

Figure 9:
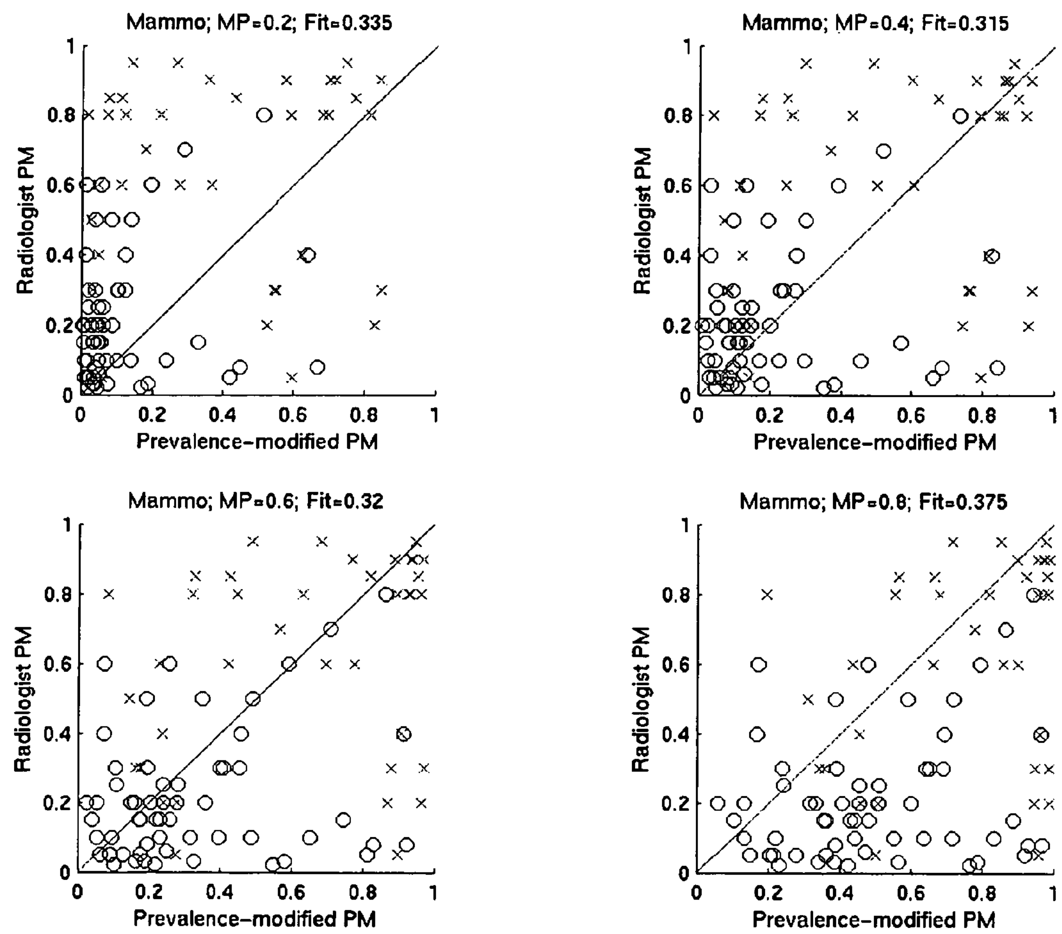
FIG. 9 illustrates least-square estimates of the relationship between the radiologist probability of malignancy and the prevalence-modified probability of malignancy for various modified prevalences and mammographic data.

FIG. 9 illustrates the relationship between the radiologist PM and the prevalence-modified PM that illustrate the least square fitting technique. Here, for example, different values of the modified prevalence are used for the mammographic data.

Figure 10:
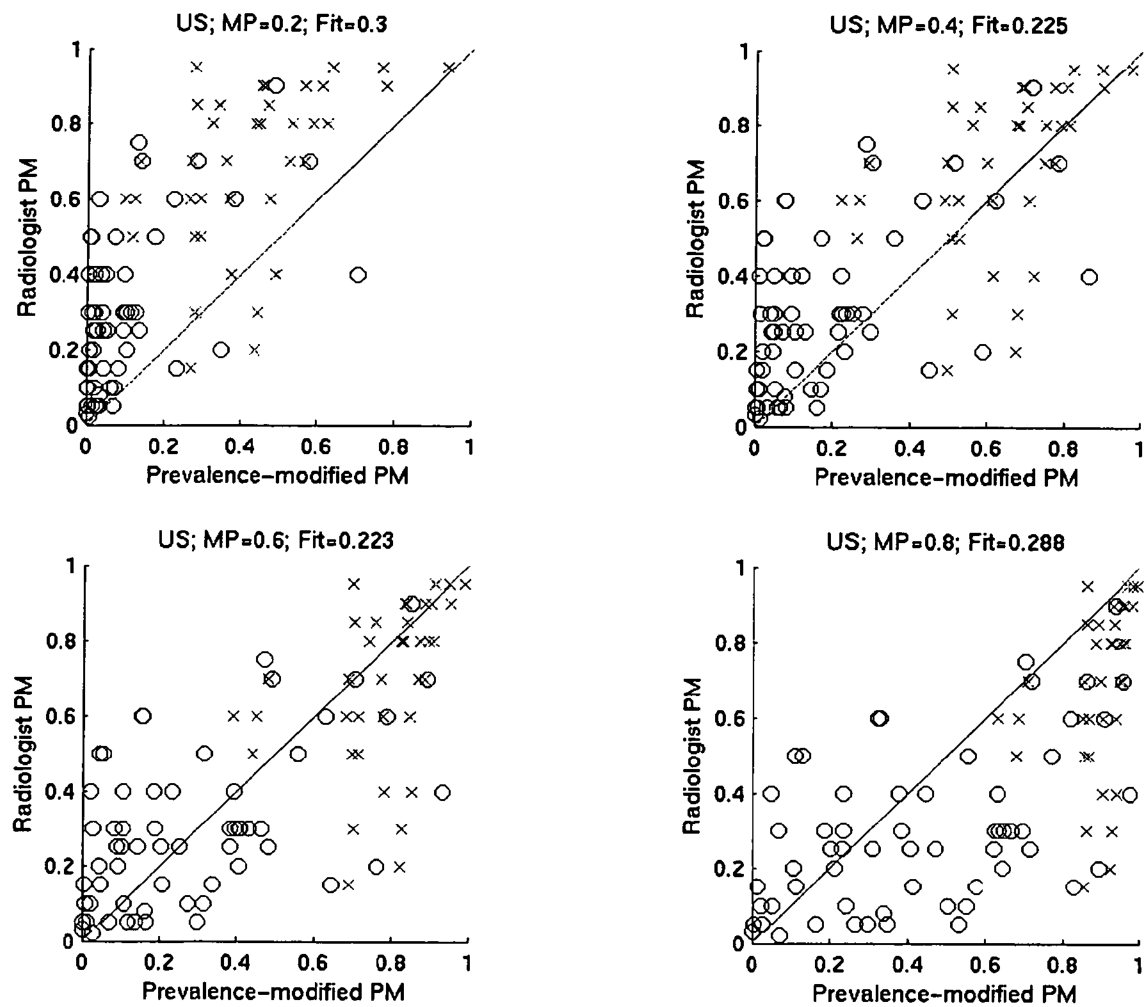
FIG. 10 illustrates least-square estimates of the relationship between the radiologist probability of malignancy and the prevalence-modified probability of malignancy for various modified prevalences and sonographic data.

FIG. 10 illustrates the relationship between the radiologist PM and the prevalence-modified PM that illustrate the least square fitting technique, along with the goodness-of-fit values. Here, for example, different values of the modified prevalence are used for the sonographic data.

Figure 11:
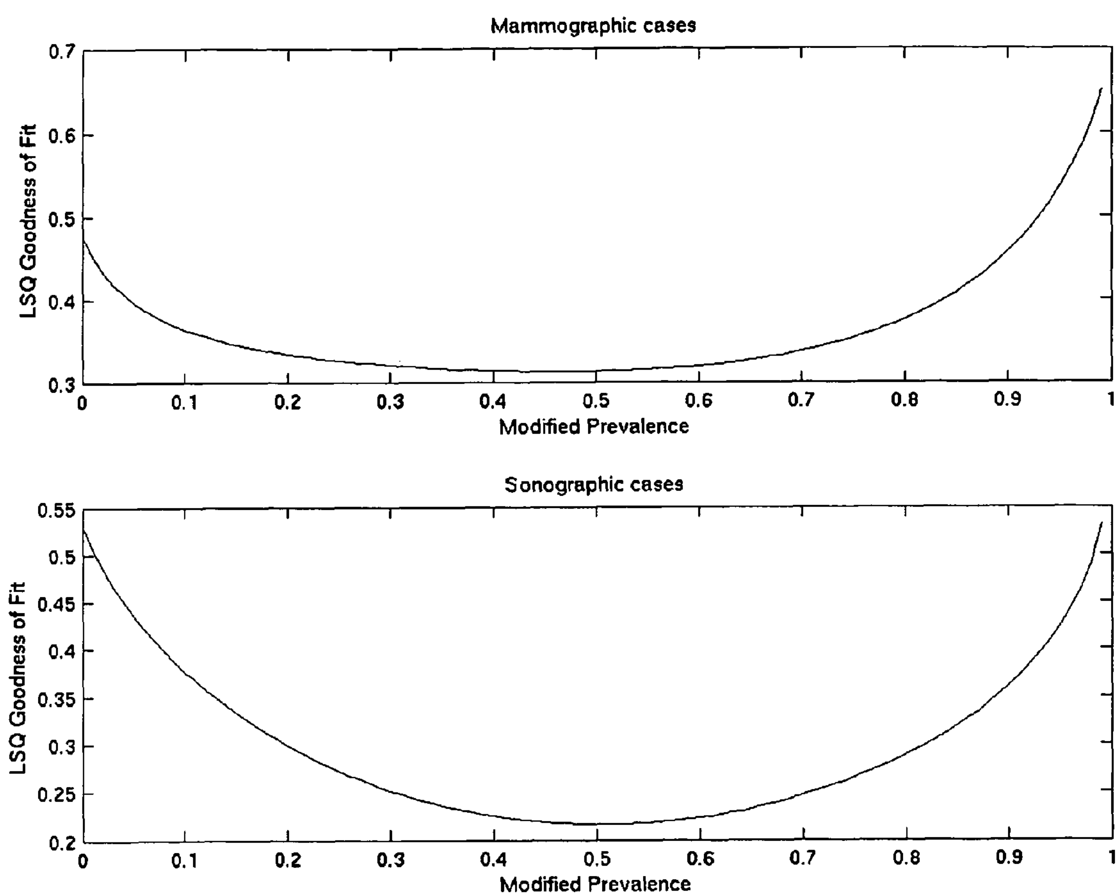
FIG. 11 illustrates the least-square estimate goodness-of-fit as a function of modified prevalence for mammographic and sonographic data.

FIG. 11 illustrates prevalence estimation from a reference set of data with known prevalence using least square curve fitting to determine the modified prevalence based on the goodness-of-fit for the mammographic and sonographic cases.

Alternatively, a general monotonic relation between the radiologist's estimates of the PM for N cases and the computer's estimates of the PM for the same N cases may be estimated.

Estimation from a reference set of data with known prevalence using averaging. An estimate of the prevalence η can be computed for each case using $$k = \frac{p_R}{R_C(1-p_R)}, \eta = \frac{k}{1+k},$$

where $p_R$ is the radiologist's probability of malignancy for that case and $R_C$ is the likelihood ratio determined by the computer's probability of malignancy for that case.

Figure 12:
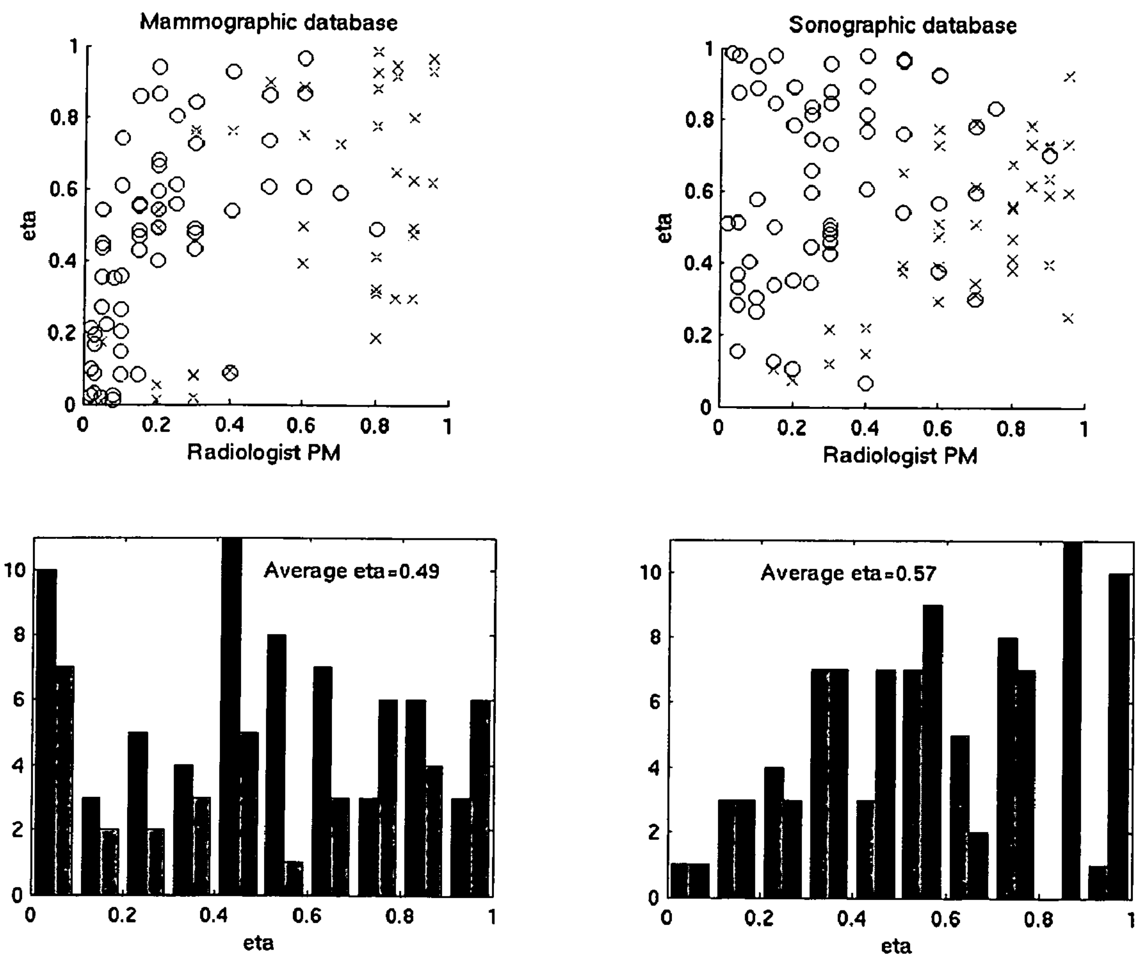
FIG. 12 illustrates the relationship between the estimated prevalence and the radiologist's probability of malignancy, as well as histograms of the estimated prevalence values, for mammographic and sonographic data.

FIG. 12 illustrates the relationship between estimated prevalence (eta) and the radiologist input PM (top) as well as the distribution of estimated prevalence values for malignant and benign lesions for the mammographic and sonographic databases (bottom).

Figure 13:
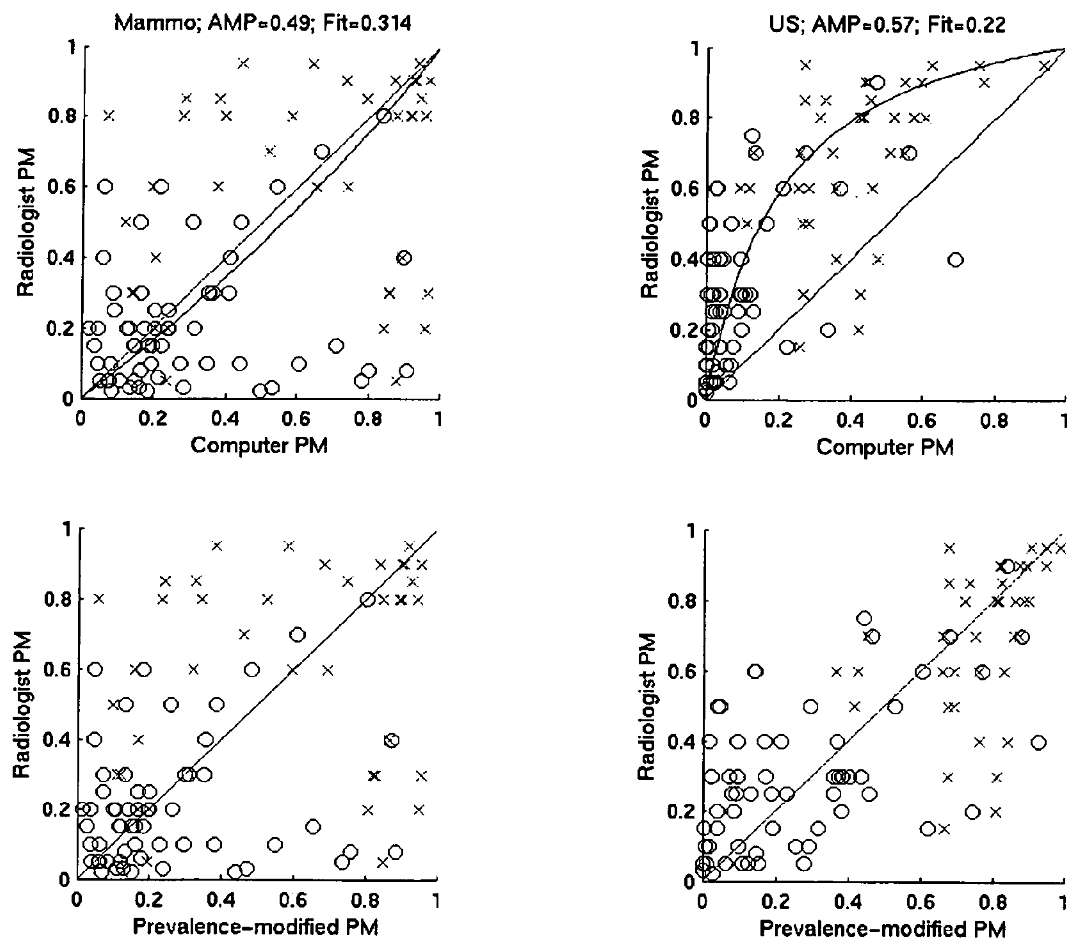
FIG. 13 illustrates averaging estimates of the relationship between the radiologist probability of malignancy and either the computer or the prevalence-modified probability of malignancy.

FIG. 13 illustrates estimates of the radiologist's prevalence by the averaging technique for the training database (k=0.55 for mammography and k=0.19 for sonography). Upper displays compare the radiologist PM to the computer output PM. Lower displays relate the radiologist PM to the prevalence-modified PM.

The curves in FIG. 13 are given by $$f(p) = \frac{Kp}{Kp+1-p}, K = \frac{k'}{k},$$

where p is the computer probability of malignancy, k' is the modified prevalence, k is the prevalence of the training database (k=0.55 for mammography and k=0.19 for sonography).

Figure 14:
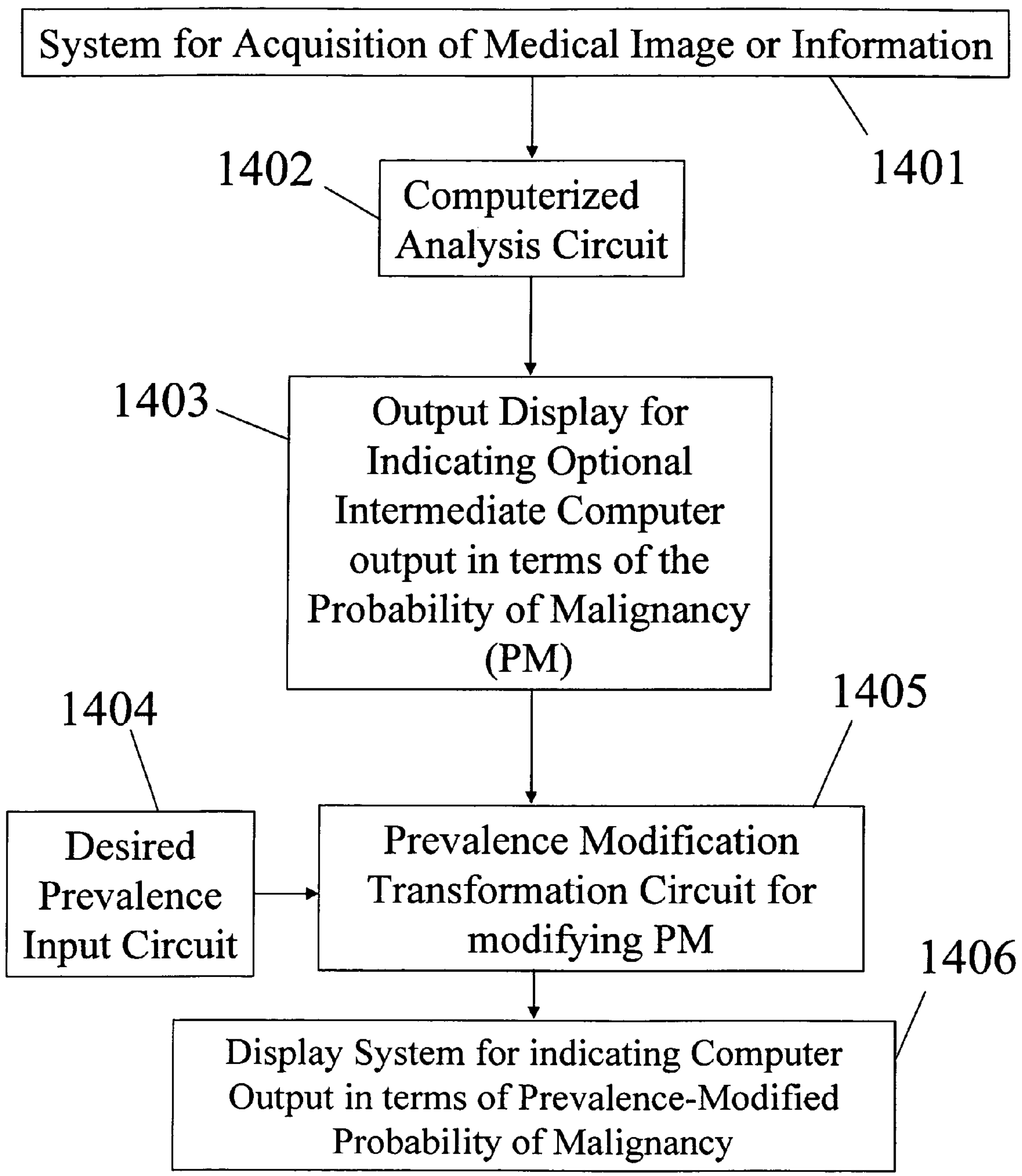
FIG. 14 illustrates a system for incorporating prevalence into the computer output in a medical diagnostic task.

FIG. 14 illustrates a schematic diagram for a system for incorporating prevalence into computer output in a diagnostic medical task. Initially, a means or system for acquiring the image data or patient information data is needed (unit 1401). This could be a mammographic unit, for example. The medical image/data information is then analyzed by a computer to yield a probability that a particular disease is present (e.g., breast cancer) by a computerized analysis circuit (unit 1402). An output device (unit 1403) is used as an option to display the computer-determined probability of disease state. Since this output may be confusing to the user, it is supplied next to a prevalence modification transformation circuit (unit 1405), which determines the modified PM based on the input desired prevalence prescribed by the desired prevalence input circuit (unit 1404). The prevalence-modified probabilities of disease status can then by displayed using a display device (unit 1406).

Figure 15:
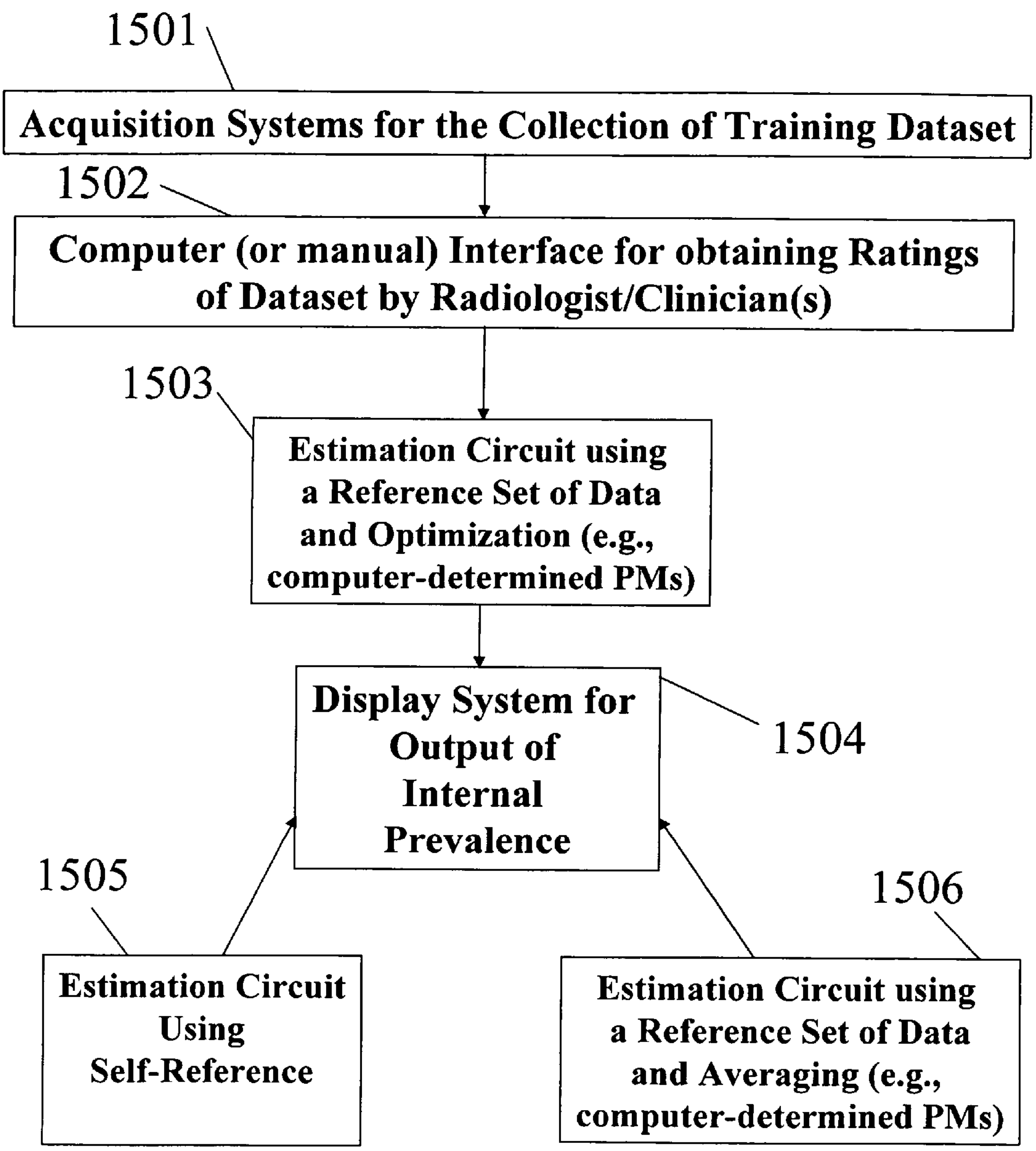
FIG. 15 illustrates a system for determining the internal prevalence of a radiology practice.

FIG. 15 illustrates a schematic diagram of a system for the determination of internal prevalence of an individual or group of individuals such as a practice of radiologists and/or clinicians. Initially, a training data set of either image data or clinical data such as biomarker results needs to be acquired by an acquisition system (unit 1501). The training data are then presented to the individual (for calibration), who provides ratings of the estimate of the probability of malignancy via a computer or manual interface (unit 1502). The ratings can then be inputted to estimation circuits that determine the internal prevalence of the individual (units 1503, 1505, and 1506). In unit 1505, the determination of internal prevalence is based only on the ratings of the individual on the training set without the need to use a reference (such as computer-determined probabilities of malignancy on some reference set of data). Units 1503 and 1506 involve the determination of the internal prevalence using a reference set. In this example, the reference set is the computerized determination of the probability of malignancy based on computer-extracted features of the lesions in question. The circuit in unit 1503 uses optimization techniques and the circuit in unit 1506 uses averaging techniques. The estimated internal prevalence (or calibration factor) is then outputted to a display system (unit 1504) for transfer to the user.

Accordingly, embodiments of the present invention include an automated method and system that employs/incorporates prevalence-based computerized analysis for computer-assisted interpretation of medical images based on computer-estimated likelihood of a pathological state, e.g., malignancy. Upon viewing an unknown mammographic case, the computer classification output is modified relative to the prevalence of the disease state that is input to the system.

It should be noted that although the method is presented on mammographic and sonographic image data sets, the intelligent workstation can be implemented for other medical images (such as chest radiography, magnetic resonance imaging, etc.) in which a computerized analysis of image or lesion features is performed with respect to some disease state.

All embodiments of the present invention conveniently may be implemented using a conventional general purpose computer or micro-processor programmed according to the teachings of the present invention, as will be apparent to those skilled in the computer art. Appropriate software may readily be prepared by programmers of ordinary skill based on the teachings of the present disclosure, as will be apparent to those skilled in the software art. In particular, the computer housing may house a motherboard that contains a CPU, memory (e.g., DRAM, ROM, EPROM, EEPROM, SRAM, SDRAM, and Flash RAM), and other optional special purpose logic devices (e.g., ASICS) or configurable logic devices (e.g., GAL and reprogrammable FPGA). The computer also includes plural input devices, (e.g., keyboard and mouse), and a display card for controlling a monitor. Additionally, the computer may include a floppy disk drive; other removable media devices (e.g. compact disc, tape, and removable magneto-optical media); and a hard disk or other fixed high density media drives, connected using an appropriate device bus (e.g., a SCSI bus, an Enhanced IDE bus, or an Ultra DMA bus). The computer may also include a compact disc reader, a compact disc reader/writer unit, or a compact disc jukebox, which may be connected to the same device bus or to another device bus.

Examples of computer readable media associated with the present invention include compact discs, hard disks, floppy disks, tape, magneto-optical disks, PROMs (e.g., EPROM, EEPROM, Flash EPROM), DRAM, SRAM, SDRAM, etc. Stored on any one or on a combination of these computer readable media, the present invention includes software for controlling both the hardware of the computer and for enabling the computer to interact with a human user. Such software may include, but is not limited to, device drivers, operating systems and user applications, such as development tools. Computer program products of the present invention include any computer readable medium which stores computer program instructions (e.g., computer code devices) which when executed by a computer causes the computer to perform the method of the present invention. The computer code devices of the present invention may be any interpretable or executable code mechanism, including but not limited to, scripts, interpreters, dynamic link libraries, Java classes, and complete executable programs. Moreover, parts of the processing of the present invention may be distributed (e.g., between (1) multiple CPUs or (2) at least one CPU and at least one configurable logic device) for better performance, reliability, and/or cost. For example, an outline or image may be selected on a first computer and sent to a second computer for remote diagnosis.

The invention may also be implemented by the preparation of application specific integrated circuits or by interconnecting an appropriate network of conventional component circuits, as will be readily apparent to those skilled in the art.

Numerous modifications and variations of the present invention are possible in light of the above teachings. It is therefore to be understood that within the scope of the appended claims, the invention may be practiced otherwise than as specifically described herein.

The invention claimed is:

1. A method for determining a probability of a disease state for a patient, comprising:

obtaining medical information including at least one of a medical image, information representative of the medical image, and information representative of a clinical examination of the patient;

calculating the probability of the disease state based on the obtained medical information;

transforming the calculated probability using a training database prevalence factor and a user-input prevalence factor indicative of the prevalence of the disease state in a population best suited to the user; and outputting the transformed probability of the disease state.

2. The method of claim 1, wherein the obtaining step comprises obtaining the medical image, and the calculating step comprises calculating the probability of the disease state based only on the obtained medical image.

3. The method of claim 1, wherein the transforming step comprises:

transforming the calculated probability using the training database prevalence factor indicative of the prevalence of the disease state in a population.

4. The method of claim 3, wherein the transforming step comprises:

transforming the calculated probability using Bayes theorem.

5. A method for determining an internal prevalence factor of a first classifier, comprising:

obtaining medical information including at least one of medical image data and information representative of the medical image data;

obtaining a first reference data set of estimates of a probability of a diseased state estimated by the first classifier based on the obtained medical information;

obtaining a second reference data set of estimates of the probability of the disease state estimated by a second classifier based on the obtained medical image information; and determining the internal prevalence factor of the first classifier based on a training prevalence factor of the second classifier, the first reference data set of estimates, and the second reference data set of estimates.

6. The method of claim 5, further comprising:

determining underlying probability densities from estimates of the first reference data set of estimates of the disease state.

7. The method of claim 6, further comprising:

applying a parameter estimation technique that includes optimization of a Bayes rule function evaluated using the determined underlying probability densities.

8. The method of claim 5, further comprising:

outputting the determined internal prevalence to a display.

9. The method of claim 5, further comprising:

determining a likelihood ratio from the first collected reference data set of estimates.

10. The method of claim 9, further comprising:

estimating the internal prevalence factor by optimizing a Bayes rule function evaluated on the determined likelihood ratio, the internal prevalence factor indicative of the prevalence of the disease state in a population.

11. The method of claim 9, further comprising:

estimating the internal prevalence factor by averaging a Bayes rule function evaluated on the determined likelihood ratio, the internal prevalence factor indicative of the prevalence of the disease state in a population.

12. The method of claim 5, wherein the determining step comprises:

determining the internal prevalence factor of a non-human, computer-based classifier.

13. An image processing system for determining a probability of a disease state for a patient, comprising:

means for obtaining medical information including at least one of a medical image, information representative of the medical image, and information representative of a clinical examination of the patient;

means for calculating the probability of the disease state based on the obtained medical information;

means for transforming the calculated probability using a training database prevalence factor and a user-input prevalence factor indicative of the prevalence of the disease state in a population best suited to the user; and means for outputting the transformed probability of the disease state.

14. The image processing system of claim 13, wherein the means for obtaining comprises means for obtaining the medical image, and the means for calculating comprises means for calculating the probability of the disease state based only on the obtained medical image.

15. The image processing system of claim 13, wherein the means for transforming comprises:

means for transforming the calculated probability using the training database prevalence factor indicative of the prevalence of the disease state in a population.

16. The method of claim 15, wherein the means for transforming comprises:

means for transforming the calculated probability using Bayes theorem.

17. A non-transitory computer readable medium storing instructions for execution on a computer, which when executed by the computer, causes the computer to determine a probability of a disease state for a patient by performing the steps of:

obtaining medical information including at least one of a medical image, information representative of the medical image, and information representative of a clinical examination of the patient;

calculating the probability of the disease state based on the obtained medical information;

transforming the calculated probability using a training database prevalence factor and a user-input prevalence factor indicative of the prevalence of the disease state in a population best suited to the user; and outputting the transformed probability of the disease state.

18. The computer readable medium of claim 17, wherein the obtaining step comprises obtaining the medical image, and the calculating step comprises calculating the probability of the disease state based only on the obtained medical image.

19. The computer readable medium of claim 17, wherein the transforming step comprises:

transforming the calculated probability using the training database prevalence factor indicative of the prevalence of the disease state in a population.

20. The computer readable medium of claim 19, wherein the transforming step comprises:

transforming the calculated probability using Bayes theorem.

* * * * *